United States Patent
Heinz et al.

(10) Patent No.: US 7,367,964 B2
(45) Date of Patent: May 6, 2008

(54) MEMBRANE SYRINGE WITH CAP

(75) Inventors: Jochen Heinz, Vendersheim (DE); Dieter Schilling, Aukrug-Innien (DE)

(73) Assignee: Transcoject Gesellschaft für medizinische Geräte mbH & Co. KG, Neumuenster (DE)

( * ) Notice: Subject to any disclaimer, the term of this patent is extended or adjusted under 35 U.S.C. 154(b) by 856 days.

(21) Appl. No.: 10/684,889

(22) Filed: Oct. 14, 2003

(65) Prior Publication Data

US 2004/0116869 A1 Jun. 17, 2004

(30) Foreign Application Priority Data

Oct. 15, 2002 (DE) ................. 102 47 963

(51) Int. Cl.
*A61M 5/00* (2006.01)
*A61M 5/31* (2006.01)

(52) U.S. Cl. ...................... 604/263; 604/243

(58) Field of Classification Search ............. 604/111, 604/93.01, 110, 195, 198, 263, 240–243, 604/192

See application file for complete search history.

(56) References Cited

U.S. PATENT DOCUMENTS

| | | | | |
|---|---|---|---|---|
| 4,220,151 A | * | 9/1980 | Whitney | 604/110 |
| 5,071,413 A | | 12/1991 | Utterberg | |
| 5,135,496 A | | 8/1992 | Vetter et al. | |
| 5,433,705 A | * | 7/1995 | Giebel et al. | 604/82 |
| 5,624,402 A | | 4/1997 | Imbert | |
| 5,883,653 A | | 3/1999 | Sasaki | |
| 5,989,227 A | | 11/1999 | Vetter et al. | |
| 6,065,270 A | | 5/2000 | Reinhard et al. | |
| 6,126,640 A | * | 10/2000 | Tucker et al. | 604/187 |
| 6,280,418 B1 | * | 8/2001 | Reinhard et al. | 604/187 |
| 6,840,291 B2 | * | 1/2005 | Caizza et al. | 141/25 |
| 6,874,522 B2 | * | 4/2005 | Anderson et al. | 137/68.3 |

* cited by examiner

*Primary Examiner*—Matthew F. Desanto
(74) *Attorney, Agent, or Firm*—McGlew and Tuttle, P.C.

(57) ABSTRACT

The syringe is a prefillable or prefilled syringe having a syringe cylinder which is delimited to one side by a plunger and which to the other side opens into a syringe connection having a free end closed by a membrane. The syringe cylinder, the syringe connection and the closing membrane are formed as one piece as a plastic injection molded part.

16 Claims, 5 Drawing Sheets

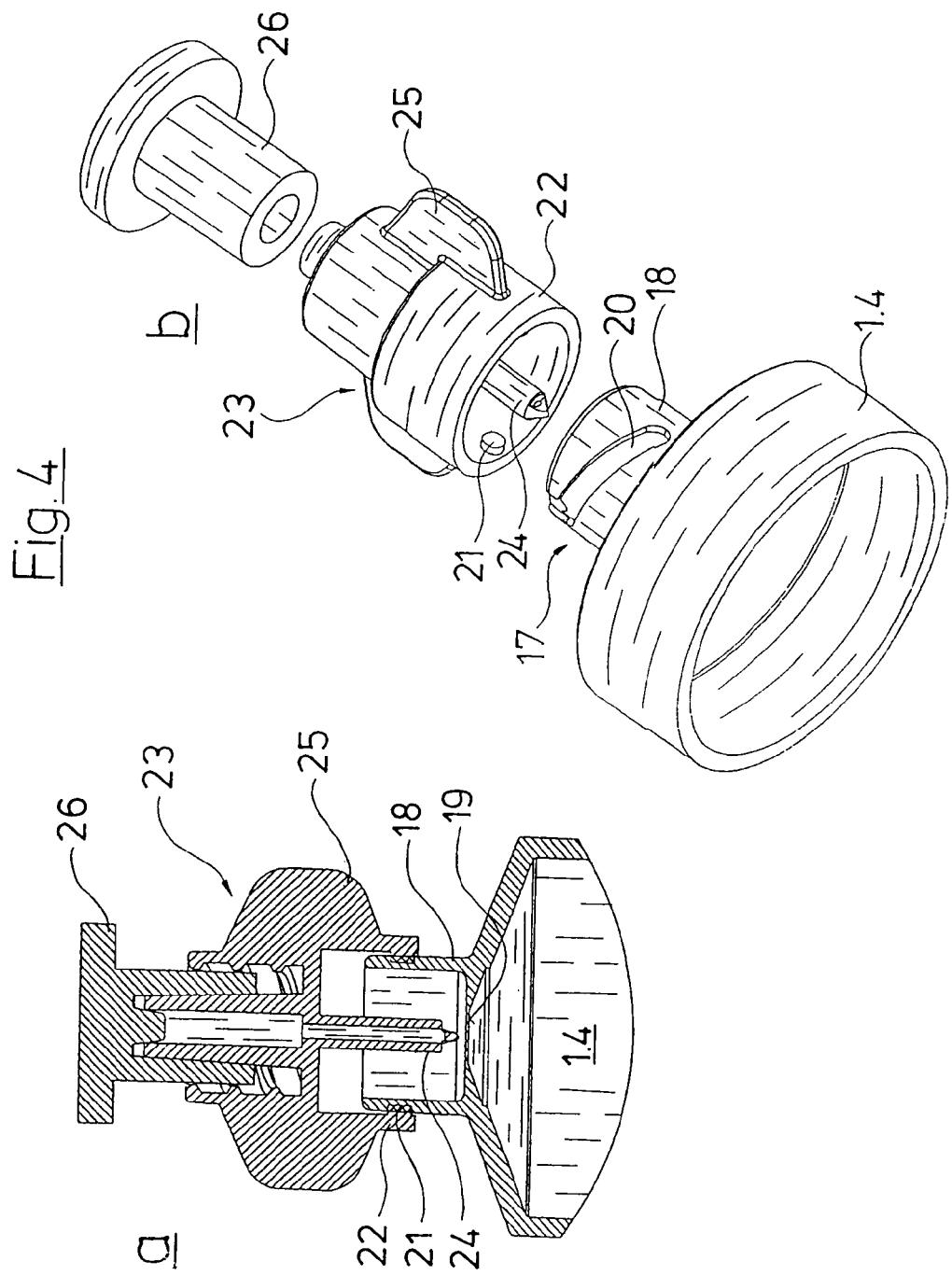

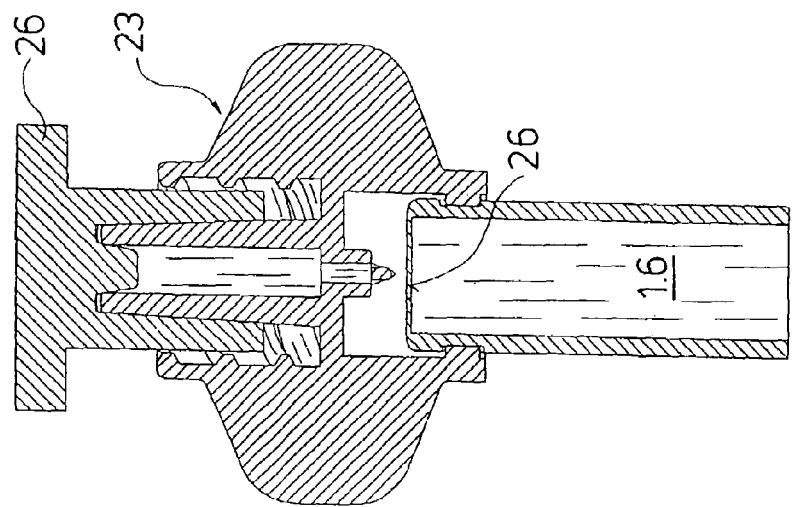
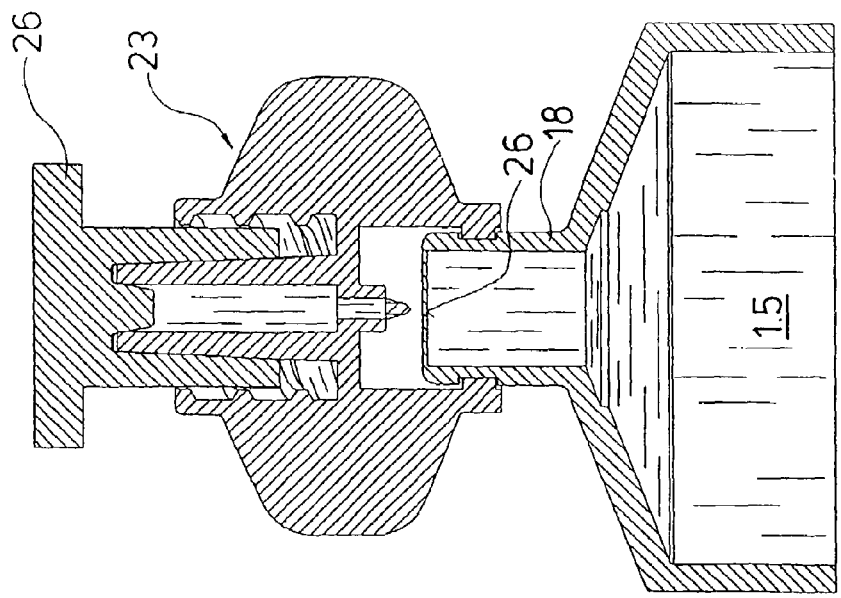

MEMBRANE SYRINGE WITH CAP

BACKGROUND OF THE INVENTION

1. Field of the Invention

The injection relates to a syringe, in particular to a prefillable or prefilled syringe, having a syringe cylinder with an end provided with a syringe connection having a free end.

2. Description of the Related Art

Prefilled syringes of this type are known; they are usually manufactured with a syringe cylinder of glass, wherein on that side of the syringe cylinder distant to the syringe plunger there is provided a syringe connection which is sealingly closed by way of a further component.

With the state of the art known from U.S. Pat. No. 5,989,227, this further component is a sealing element which is rigidly connected to and is to remain on the syringe connection. For removing the fluid located in the syringe cylinder this closure must be pierced by way of a cannula. The solution known from U.S. Pat. No. 5,135,496 is more favorable inasmuch as this further component already has a through-bore which at the end is sealed by way of a closure plug which must first be directly removed before use. The embodiment form described here however is extremely complicated in its construction since apart from the syringe cylinder three or four further components are required.

U.S. Pat. No. 5,833,653 discloses a syringe connection which is closed by way of a further component which although comprising a central through-bore, is however closed by way of a membrane. In order to release this connection the syringe cylinder is pressed in, by which means the membrane is deflected outwards due to the increased inner pressure, and here is pierced by a spike-like plug which projects into the Luer connection of the syringe. Disregarding the fact that this solution is also complicated in its design due to the multitude of components, the design of the membrane is very difficult with regard to manufacturing technology and is thus expensive. Specifically it needs to be thin enough such that with the impingement of pressure it bulges sufficiently towards the spike, and on the other hand it must be thick enough to reliably close off the contents.

For syringes with a syringe cylinder consisting of plastic, a similar closure variant is known from U.S. Pat. No. 5,624,402. The closure element to be placed onto the syringe connection likewise consists of a multitude of components and requires a costly manufacture and is thus expensive.

SUMMARY OF THE INVENTION

Against this background it is the object of the invention to create a syringe according to the known type, which is inexpensive and may be easily manufactured, but which at the same time however ensures a sealed closure of the fluid located therein.

The basic concept of the present invention is to design the syringe cylinder together with the syringe connection and the membrane closing this as one piece as a plastic injection molded part. By way of this the multitude of parts which is otherwise common is minimized, by which means the manufacturing costs may be reduced to a minimum, in particular with the large batch numbers produced here. At the same time the design according to the invention also offers a large safety with regard to sealing, since with the selection of a suitable, diffusion-tight plastic only the region between the plunger and the syringe cylinder remains to be sealed. This region must be sealed with all syringe designs and this has been technically mastered and may be realized with relatively little cost with regard to manufacturing technology. A further advantage of the membrane closure manufactured of one piece with the syringe is that the content, which is typically a medicine, only comes into contact with one and the same plastic. Furthermore it is also advantageous that the syringe is completely tight also with all subsequent processing steps such as autoclaving, labeling etc. and is not compromised by way of these steps. The sealing can be checked visually so that the sterility is considerably simpler to verify than is the case with the state of the art.

A syringe connection within the context of the invention is to be understood as the connection provided at the that end of the syringe which is distant to the plunger, which is either a Luer connection or a Luer lock connection, but also a special connection onto which then a component is placed which forms the actual cannula or other closure.

The syringe according to the invention, at the free end of the syringe connection is preferably provided with a cap which comprises a spike for piercing the membrane. At the same time it is particularly favorable if the cap is designed such that it at least engages over the free end of the syringe connection in order to protect the whole syringe connection from germs and simultaneously to form a tool with which the membrane may be pierced in a directed manner, and thus the syringe may be opened for the directed application.

It is particularly advantageous if the cap and the syringe are matched to one another such that the cap is arranged in a first position in which the spike lies opposite the membrane and arranged at a distance to this. In this position the cap merely serves for protecting the syringe connection. From this position the cap may be brought into a second position in which the spike penetrates through the membrane. In this manner the membrane may be pierced, i.e. the syringe may be opened for its directed use without having to remove the cap from the syringe, by which means the danger of contamination with germs is reduced further since the spike which after opening the usually sterile package likewise lies sterile in the inside of the cap, then without further removal may be introduced directly into the membrane. Only afterwards is the cap removed as the case may be, in order to connect the syringe.

The invention however envisages design variants which will be described further below and with which the cap after piercing the membrane, is not to be removed but simultaneously forms a connection component. Such a component may for example be formed by a tubular spike which opens into the inside of a Luer connection or Luer lock connection provided on the outer side of the cap. With such a design the cap usefully at its cannula-side end is yet provided with a (further) protective cap which engages over at least the Luer connection and closes this to the outside. With the application of a Luer lock connection on the outer side this may either be completely engaged over by the protective cap or however in a manner such that the Luer connection which is always formed within the Luer lock connection is engaged over.

If the cap as is envisaged in a further formation of the invention is formed as a further component not only for opening the membrane, but also for leading through the fluid located in the syringe, then this cap may usefully be connected to the syringe cylinder by way of a bayonet, wherein the bayonet is designed such that the cap engages over the syringe connection, and the actual bayonet path has a gradient in a manner such that with the transfer from the first into the second position the cap is moved axially in the direction of the syringe cylinder. This bayonet path with a gradient then at the same time forms the path guide for a targeted penetration of the spike into the membrane, wherein here one may create a relatively high pressure with a relatively small force of the hand, depending on the gradient. This permits a relatively thick design of the membrane which in turn is favorable with regard to manufacturing technology.

Instead of the previously mentioned intermediate component, thus a cap with a through-flow function, the syringe connection according to the invention may also be directly formed as a Luer connection or preferably as a Luer lock connection, wherein the membrane preferably only closes the Luer connection so that the thread present in the Luer lock connection may be used for fastening and for a guide path.

In order to prevent the cap from being unintentionally brought from the first into the second position, it is useful to provide locking means between the cap and the syringe connection or syringe cylinder, which ensures that one needs to overcome a predefined force for conveying from the first into the second position. Such locking means for example may be formed by a ring tapering conically towards the tip on the outer circumference of the Luer lock connection, or corresponding ring sections which engage into a corresponding groove or groove section on the inner circumference of the cap. The cap is preferably formed divided in this region so that the remaining circumferential parts may spring outwards in order to overcome this ring. Such a conically tapering ring on the outer circumference of the Luer lock connection furthermore has the advantage that not only cannula but where appropriate a flexible tubing may be directly connected to this syringe closure in that this tubing is pushed over the ring. The conicity of the ring not only encourages the sliding on of the flexible tuning, but also at its outer circumference provides for an increased sealing effect which as a rule is sufficient for a reliable sealing between the flexible tubing and the syringe body.

The syringe, in particular the syringe cylinder with the membrane which are formed as one piece at the same time are advantageously manufactured of polyolefins, preferably of polypropylene (PP) or cyclo-olefin polymers (COP) or other barrier plastics.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

FIG. 2a the cannula-side end of a syringe cylinder of a syringe according to the invention with a placed-on cap, in a first position and in a longitudinal section;

FIG. 2b the cap in a longitudinal section;

FIG. 2c the cannula-side end of the syringe cylinder in a longitudinal section;

FIG. 2d the cannula-side end of the syringe cylinder with a placed-on cap in the second position, in a longitudinal section;

FIG. 2e a lateral view of the embodiment shown in FIG. 2a;

FIG. 3a a longitudinal section of the cap and the cannula-side end of the syringe cylinder in the first position;

FIG. 3b a longitudinal section of the cap;

FIG. 3c a longitudinal section of the cannula-side end of the syringe cylinder;

FIG. 3d the cannula-side end of the syringe cylinder with a cap in the second position, in a longitudinal section;

FIG. 3e a lateral view of the cap;

FIG. 3f a lateral view of the cannula-side end of the syringe cylinder;

FIG. 3g a lateral view of the two components in a first position;

FIG. 4 a fourth embodiment variant with an intermediate component, and specifically;

FIG. 4a a longitudinal section of one variant of the cannula-side end of the syringe cylinder with a placed-on intermediate component in a first position, with a protective cap;

FIG. 4b the previously mentioned components in an exploded representation;

FIG. 5 a longitudinal section of one variant of the cannula-side end of the syringe cylinder with a placed-on intermediate component, in a first position, with a protective cap; and FIG. 6 a longitudinal section of a further variant of the cannula-side end of the syringe cylinder with a placed-on intermediate component in a first position with a protective cap.

DETAILED DESCRIPTION OF THE PRESENTLY PREFERRED EMBODIMENTS

Figure 1:
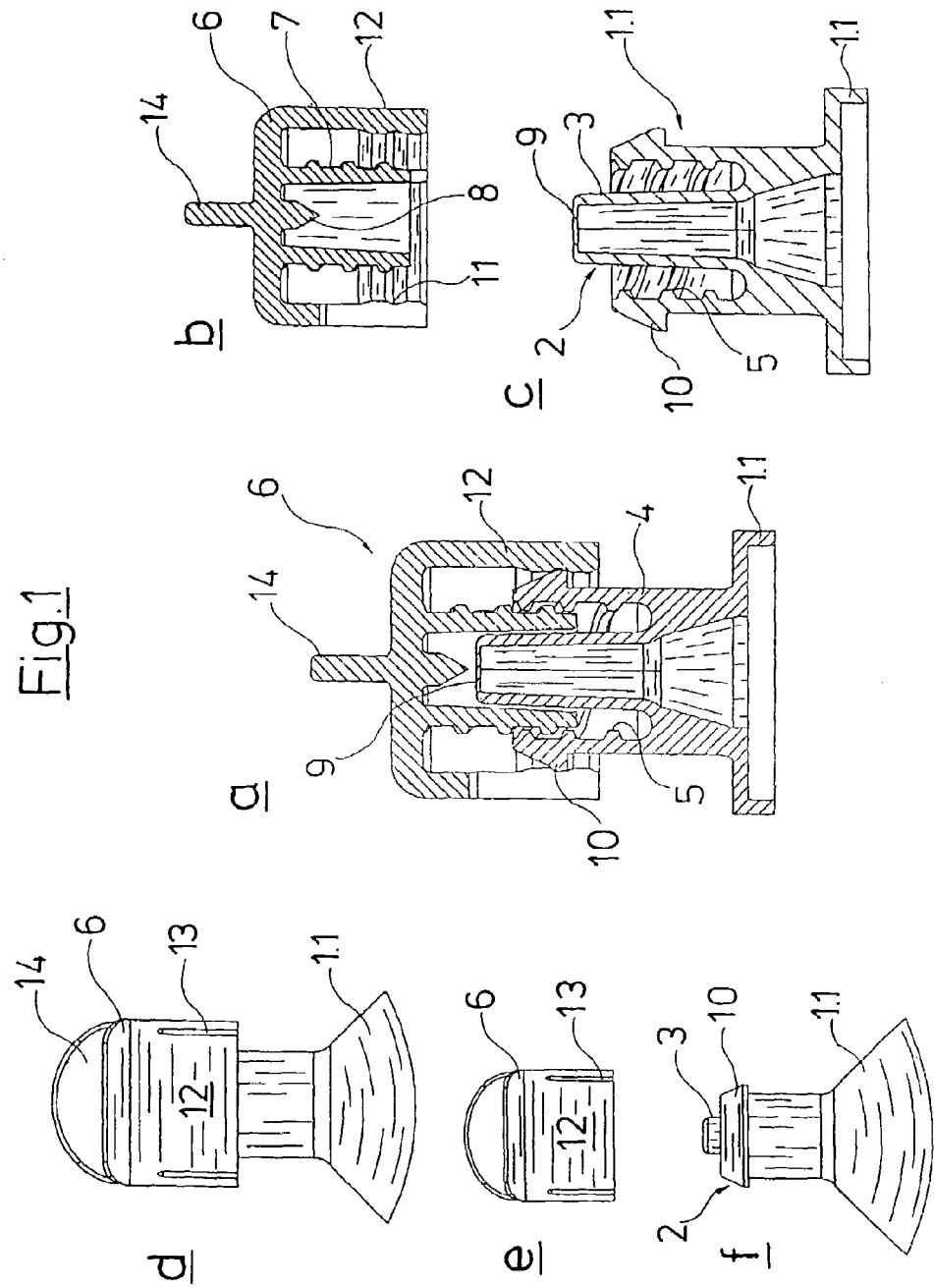
FIG. 1a is a longitudinal section of the cannula-side end of a syringe cylinder of a syringe according to the invention with a placed-on cap, in a first position.
FIG. 1b is a longitudinal section of the cap.
FIG. 1c is a longitudinal section of the cannula-side end of the syringe cylinder.
FIG. 1d is a side view of the cannula-side end of the syringe cylinder with a placed-on cap.
FIG. 1e is a side view of the cap.
FIG. 1f is a side view of the cannula-side end of the syringe cylinder.

With the embodiment form according to FIG. 1 a Luer lock connection 2 is integrally formed onto the cannula-side end of the syringe cylinder which is not shown in detail. The Luer lock connection 2 in the known manner consists of a Luer connection 3 which at a distance is surrounded by a cylindrical wall section 4 on whose inner side there is provided a thread 5.

For protecting the syringe connection formed by the Luer lock connection 2 there is provided a cap 6 which is formed essentially cup-shaped and comprises an inner cylinder 7 which carries an outer thread which may be brought to engage with the thread 5 of the Luer lock connection 2. Within the inner cylinder 7 there is provided a spike 8 which in a first position according to FIG. 1a is arranged at a small distance to a membrane 9 which closes the Luer connection 3 and seals it to the top. As is clearly evident from FIGS. 1a and c the syringe cylinder, Luer lock connection 2 as well as the membrane 9 are formed as one piece and specifically as an injection molded plastic part.

So that the cap 6 remains in its first position shown in FIG. 1a in which the spike 8 is arranged at a distance to the membrane 9, there are provided locking means, and specifically in the form of a ring 10 which tapers conically towards the tip and which is integrally formed on the outer circumference of an outer cylinder 12 of the cap 6. The outer cylinder 12 which is arranged at a distance to the inner cylinder 7 and is arranged surrounding this as well as the end-side part of the wall section 4, has in total four longitudinal recesses 13 distributed over the circumference, so that the outer cylinder sections formed by way of this, for placing on the cap 6 into the first position shown in FIG. 1a, may overcome the ring 10 until this ring lies in the groove 11. In this position, as FIG. 1a clearly shows, the inner cylinder 7 is immersed up to roughly half into the thread 5 of the Luer lock connection 2, so that on the one hand there is provided a stable seating as well as a mechanical protection of the Luer lock connection, and on the other hand there still remains a free path in order to bring the cap 6 into a second position in which after overcoming the locking means 10, 11 the spike 8 is completely immersed into the membrane 9 and thus in order to open the lumen of the Luer connection 3. A grip piece 14 is provided on the upper side of the cap in order to bring the cap 6 into this position.

The syringe according to the invention is prefilled at the factory and at the end distant to the cannula is provided with a plunger in a manner known per se. The cannula end 1.1 is provided with the cap 6, and specifically in the first position as is shown in FIG. 1a. The syringe which is thus completed is packed in a sterile manner. For use firstly the sterile package is opened for the first time, whereupon the user grips the cap 6 at the grip piece 14 and from this first position screws it in whilst completely overcoming the locking force, i.e. up to the abutment, into the thread 5 of the Luer lock connection 2. At the same time the thread 5 serves for guiding as well as force transmission. The spike 8 at the same time works its way into the membrane 9 and opens the lumen of the Luer connection 3. By rotating in the opposite direction the cap is then removed and a cannula preferably with a Luer lock connection is fastened in a manner known per se. Alternatively via the wall section 4 one may also directly connect a flexible tubing, with this then the ring 11 tapering conically towards the tip serves as a guide as well as a sealing ring.

Figure 2:
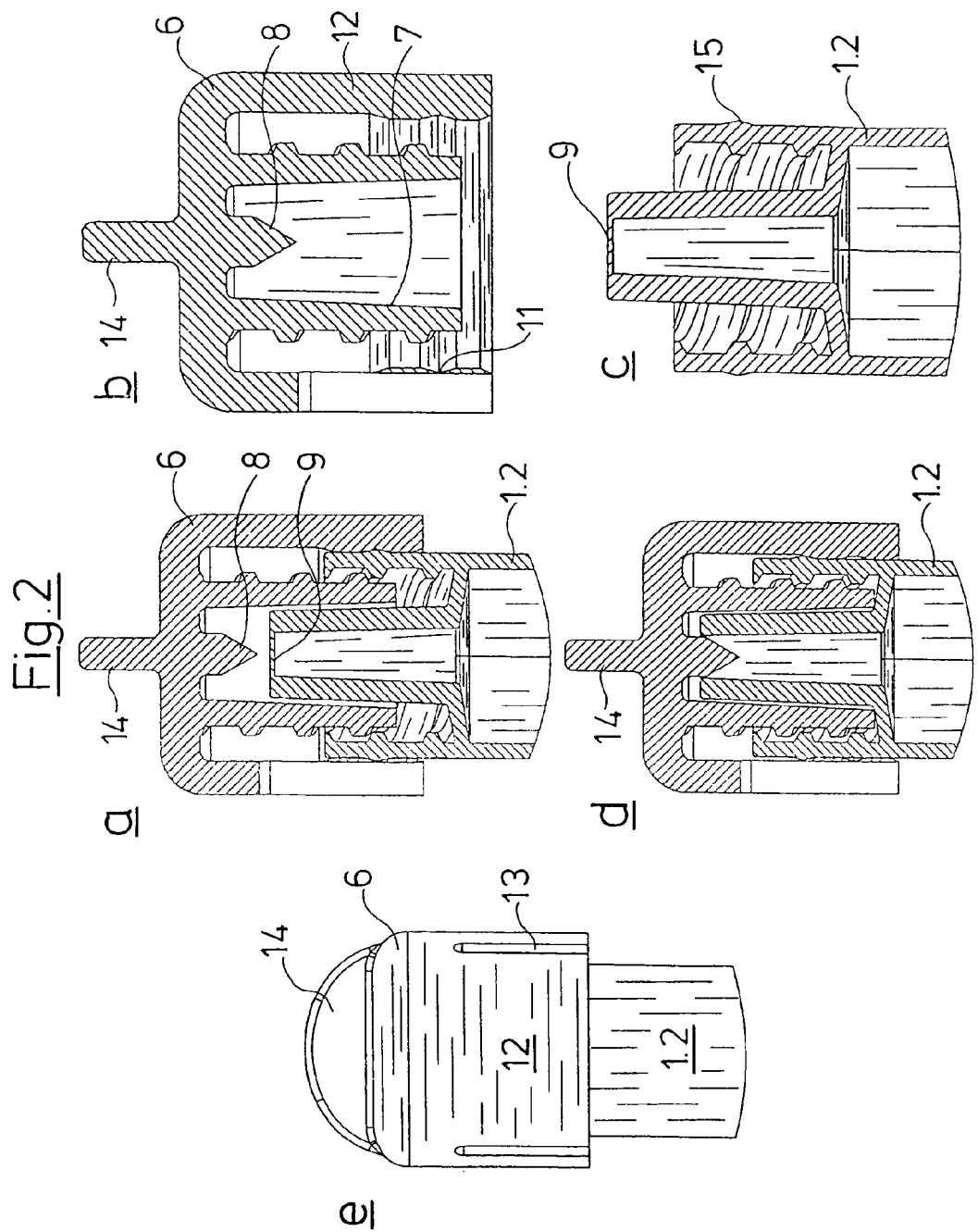
FIG. 2 an alternative embodiment, and specifically

The embodiment variant according to FIG. 2 differs from that previously described in that here there is provided no conically tapering ring 10, but instead of this a locking projection 15 is formed on the outer side of the wall section 4, and this projection lockingly cooperates with the groove 11 in the same manner as with the embodiment variant according to FIG. 1. In FIG. 2 there are shown the first position in which the spike 8 is arranged lying opposite the membrane at a distance, in the representation according to FIG. 2a, and the second position in which the spike 8 has completely penetrated through membrane 9 and has penetrated into the Luer connection 3 at the end face. At the same time the end-face free end of the inner cylinder 7 bears on the abutment, specifically on the base of the Luer lock connection 2.

The cannula end 1.2 of the syringe is shown somewhat differently than in FIG. 1, in order by way of example to emphasize that here it may be the case of a cannula end of any syringe.

Figure 3:
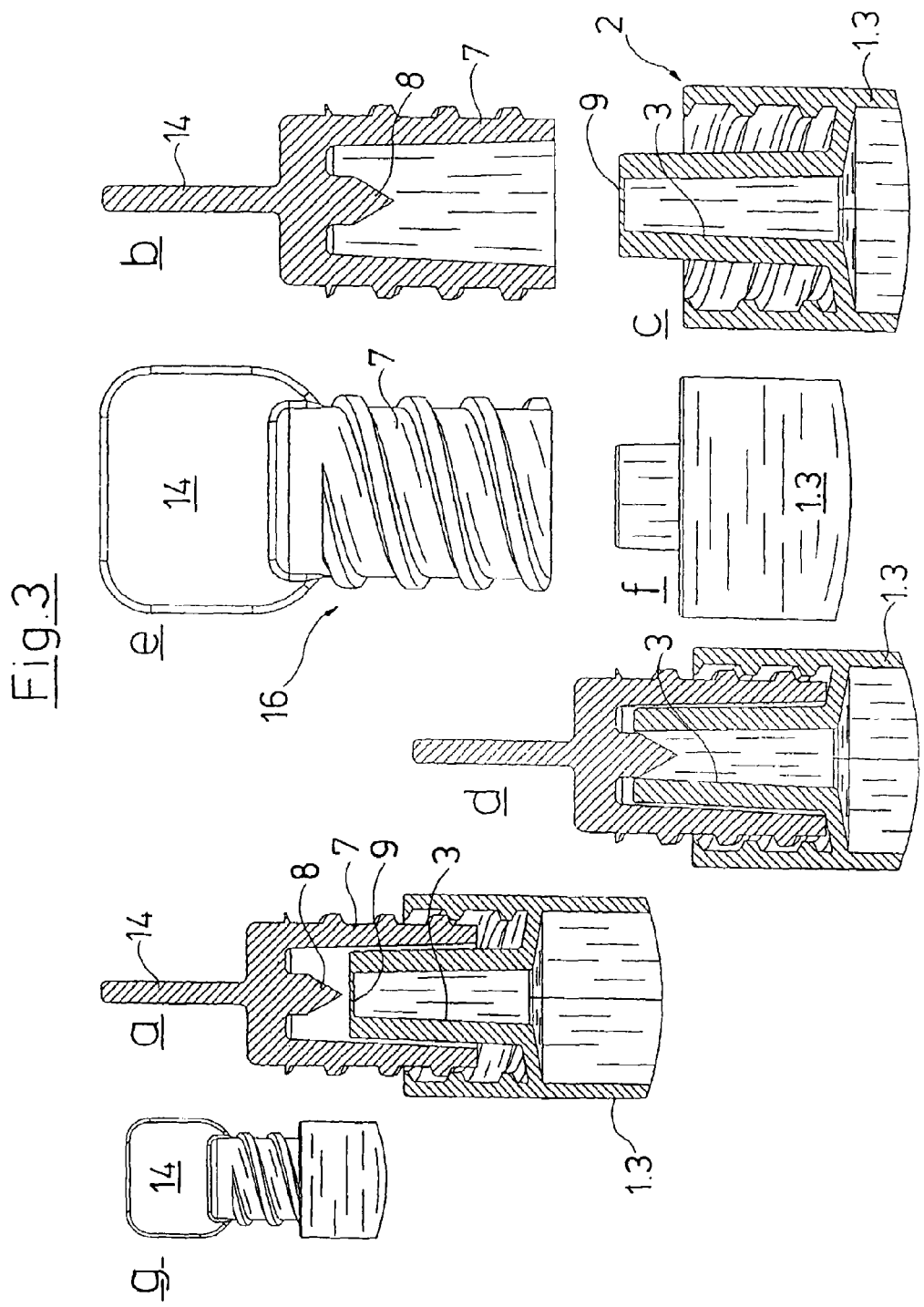
FIG. 3 a third embodiment variant and specifically.

By way of FIG. 3 there is shown a third embodiment variant which differs from that previously described by way of FIG. 2 essentially at the cap side. Specifically there is provided a cap 16 here which consists of the inner cylinder 7, the spike 8 as well as the grip piece 14 and a corresponding end-face connection wall. Since here the cap 16 merely engages over the Luer connection 3 and no outer cylinder is provided, the locking means here are also done away with. On the outer circumference of the wall section 4 there is neither provided a locking projection nor a ring. Irrespective of this the cannula ends 1.1 and 1.2 described previously by way of FIGS. 1 and 2 respectively may be used with the simplified cap 16 according to FIG. 3.

With the embodiment form according to FIG. 4 the cannula end 1.4 of the syringe cylinder opens into a syringe connection 17 which in contrast to the previously described embodiment forms is not formed by a Luer lock connection but by a cylinder connection 18 which at its end proximal to the syringe cylinder comprises a membrane 19. On the outer side of the cylinder section 18 there are integrally formed two grooves 20 displaced by 180° to one another with a thread-like gradient. Guide studs 21 engage into these grooves 20 and these studs are displaced to one another likewise by 180° on the inner circumference of the cylinder section 22 which forms part of an intermediate component 23 which on the cannula-side is provided with a Luer lock connection 2. The Luer lock connection 2 is connected by an end-face wall to the cylinder section 22 on which a hollow spike 24 is integrally formed, whose inner channel is connected to the lumen of the Luer connection 3 of the Luer lock connection 2. On the outer side of the intermediate component 23 there are provided two grip pieces likewise displaced by 180° which serve the handling of the component and whose shape and arrangement are to be deduced in detail from FIG. 4.

A protective cap 26 which is pushed on as is evident from FIG. 4a protects the Luer connection 3. This protective cap with a blunt spike engages into the lumen of the Luer connection 3.

The prefilled syringe is supplied as is shown in FIG. 4a, i.e. the intermediate component 23 is located in a first (upper) position of the grooves 20. The guide bolts 21 thus already lie in the grooves 20 so that the cylinder section 22 with its inner circumference is led on the outer circumference of the cylinder section 18. The protective cap 26 covers the Luer connection 3 of the Luer lock connection 2. For opening the membrane 19 the intermediate component 23 is gripped by way of the grip pieces and rotated along the grooves 20 into the second position. By way of the fact that the grooves 20 run obliquely from the top to the bottom (with respect to FIG. 4), then by rotating the intermediate component 23 this is lowered with respect to the cannula end or approaches this end. At the same time the hollow spike 24 pierces the membrane 19 and thus creates a fluid-leading connection between the inside of the syringe cylinder and the lumen of the Luer connection 3. Then only the protective cap 26 is to be removed, whereupon a cannula may be attached and the syringe may be used it its directed manner.

Two further embodiment variants of the invention are yet shown by way of FIGS. 5 and 6, and specifically with regard to the cannula end of the syringe cylinder 1.5 and 1.6 respectively. The intermediate component 23 as well as the protective cap 26 with this are identical (disregarding the length of the hollow spike) to the designs described by way of FIGS. 4a and 4b.

In contrast to the cannula end of the syringe cylinder 1.4, with the syringe cylinder 1.5 the membrane 27 is not arranged at the base of the cylinder section 18, but at the upper end of this. This has the advantage that a smooth ending without rear projecting parts arises which is easily handled. Furthermore the possible filling volume of the syringe cylinder is increased and the length of the hollow spike 24 is shortened. This also applies to the embodiment variant represented by way of FIG. 6 with which the cannula end of the syringe cylinder 1.6 merges into the syringe cylinder in a flush manner. This variant is to particularly emphasize the fact that the invention may be applied with syringe cylinder of almost any shape.

The previously described embodiment examples are only to be understood as examples and are not limiting. The previously described features may also be applied individually or in a varying combination. In a simplified embodiment e.g. a Luer connection provided with a membrane may also be provided which may be opened by way of a cap able to be placed on, or other suitable tool.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A syringe comprising:
   a syringe cylinder having an end;
   a syringe connection provided on said end of said syringe cylinder, said syringe connection having a free end, said syringe connection including a lock connection having an internal thread, said lock connection including a ring, said ring tapering conically toward said free end;
   a cap, said cap engaging said free end of said syringe connection, said cap having an external thread, said external thread engaging said internal thread of said lock connection, said ring retaining said cap in a first position such that force is required to move said cap from said first position to a second position; and
   a membrane closing said free end of said syringe connection, said cap having a spike for piercing said membrane, wherein said syringe cylinder, said syringe connection, and said membrane are formed as one piece of injection molded plastic.

2. A syringe as in claim 1, wherein said cap is movable from a first position, where said spike is arranged opposite said membrane, to a second position, where said spike pierces said membrane.

3. A syringe as in claim 2, wherein said cap comprises a Luer connection having an inside, said spike being formed as a tube which communicates with said inside of said Luer connection.

4. A syringe as in claim 3, further comprising a removable protective cap which engages over said Luer connection.

5. A syringe as in claim 2, wherein one of said cap and said syringe connection is provided with at least one groove with a thread-like axial gradient, and the other of said cap and said syringe connection is provided with at least one stud which engages in a respective at least one groove, thereby providing a bayonet connection for moving said cap from said first position to said second position.

6. A syringe as in claim 2, further comprising means for retaining said cap in said first position so that force is required to move said cap from said first position to said second position.

7. A syringe as in claim 1, wherein said syringe connection comprises a Luer connection, said membrane closing only said Luer connection.

8. A syringe comprising:
   a syringe cylinder;
   a syringe connector element connected to said syringe cylinder, said syringe connector element having a conically tapered ring;
   a membrane, said membrane being integrally connected to said syringe connector element to form a unitary syringe cylinder structure, wherein said syringe cylinder, said syringe connector element and said membrane are formed as one piece of injection molded plastic; and
   a cap, said cap being flexible to generate a snap in retaining function as said cap moves over said ring of said syringe connector element, said cap being connected to said syringe connector element via said ring.

9. A syringe as in claim 8, wherein ring retains said cap in a first position such that force is required to move said cap from said first position to a second position.

10. A syringe as in claim 9, wherein said cap has a spike for piercing said membrane.

11. A syringe as in claim 10, wherein said syringe connection includes a lock connection having an internal thread, said cap having an external thread, said external thread engaging said internal thread of said lock connection.

12. A syringe as in claim 8, wherein said cap has a spike for piercing said membrane.

13. A syringe as in claim 12, wherein said cap is movable from a first position to a second position, said spike being opposite said membrane in said first position, said spike engaging said membrane in said second position such that said spike pierces said membrane.

14. A syringe as in claim 8, wherein said syringe connection includes a lock connection, said lock connection having an internal thread, said cap having an external thread, said external thread engaging said internal thread of said lock connection.

15. A syringe as in claim 8, wherein said cap is movable from a first position to a second position, said spike being opposite said membrane in said first position, said spike engaging said membrane in said second position such that said spike pierces said membrane.

16. A syringe as in claim 8, wherein said syringe connection includes a Luer connection, said membrane closing said Luer connection.

* * * * *